(12) United States Patent
Romano et al.

(10) Patent No.: US 10,086,369 B2
(45) Date of Patent: Oct. 2, 2018

(54) CLOSED CIRCUIT STERILE DEVICE AND METHOD OF COLLECTION, TRANSPORT AND PROCESSING IN TOTAL STERILE CHAIN

(71) Applicant: 4I S.R.L., Milan (IT)

(72) Inventors: Carlo Luca Romano, Milan (IT); Lorenzo Drago, Milan (IT); Tommaso Brenicci, Milan (IT); Marco Bertoni, Milan (IT)

(73) Assignee: 4I S.R.L., Milan (IT)

( * ) Notice: Subject to any disclaimer, the term of this patent is extended or adjusted under 35 U.S.C. 154(b) by 170 days.

(21) Appl. No.: 15/313,811

(22) PCT Filed: May 22, 2015

(86) PCT No.: PCT/IT2015/000140
§ 371 (c)(1),
(2) Date: Nov. 23, 2016

(87) PCT Pub. No.: WO2015/177821
PCT Pub. Date: Nov. 26, 2015

(65) Prior Publication Data
US 2017/0136454 A1    May 18, 2017

(30) Foreign Application Priority Data
May 23, 2014 (IT) .............................. RM2014A0270

(51) Int. Cl.
*B01L 3/00* (2006.01)
*A61B 50/31* (2016.01)
(Continued)

(52) U.S. Cl.
CPC .............. *B01L 3/502* (2013.01); *A61B 50/31* (2016.02); *A61B 50/33* (2016.02); *A61B 50/36* (2016.02);
(Continued)

(58) Field of Classification Search
CPC .......... B01L 3/502; B01L 3/5025; A61L 2/18; A61F 2/0095; A61B 50/31
See application file for complete search history.

(56) References Cited

U.S. PATENT DOCUMENTS 3,163,160 A    12/1964  Cohen
5,869,003 A     2/1999  Nason
(Continued)

OTHER PUBLICATIONS

Lorenzo Drago, et al., "Use of Dithiothreitol to Improve the Diagnosis of Prosthetic joint Infections", J. Orthop. Res 31:1694-1699, Jul. 2, 2013.

*Primary Examiner* — Sean E Conley
(74) *Attorney, Agent, or Firm* — Muncy, Geissler, Olds & Lowe, P.C.

(57) ABSTRACT

The present invention concerns a sterile closed loop device for medical-surgical use intended for the collection, the transportation and the processing of prostheses and/or biological samples and the like, having at least one collection compartment provided with an hermetically closable main opening, for the introduction of said prosthesis and/or biological samples and the like to be analyzed, so as to be contained in it, at least one containment chamber, in which a solution is contained for the chemical detachment of bacteria adhering to animate or inanimate surfaces, such as prostheses and the like, and/or bacterial biofilm, said containment chamber being selectively communicating with said collection compartment, so that said solution can be conveyed from said containment chamber to said collection compartment, for the chemical separation of bacteria to said prosthesis and/or biological samples and the like to be analyzed, that can be inserted in said collection compartment, and extraction means of said solution for the chemical detachment of bacteria from said collection compartment. The present invention also concerns a method for collecting, (Continued)

transporting and processing a prosthesis and/or biological samples and the like to be analyzed.

18 Claims, 4 Drawing Sheets (51) Int. Cl.
*A61B 50/33* (2016.01)
*A61B 50/36* (2016.01)
*A61F 2/00* (2006.01)
*A61L 2/18* (2006.01)
*C12Q 1/04* (2006.01)
*G01N 1/00* (2006.01)
*G01N 1/40* (2006.01)
*A61B 50/00* (2016.01)

(52) U.S. Cl.
CPC .............. *A61F 2/0095* (2013.01); *A61L 2/18* (2013.01); *B01L 3/5025* (2013.01); *C12Q 1/04* (2013.01); *A61B 2050/0057* (2016.02); *A61L 2202/21* (2013.01); *B01L 2200/18* (2013.01); *B01L 2300/047* (2013.01); *B01L 2300/087* (2013.01); *B01L 2300/123* (2013.01); *B01L 2400/0481* (2013.01); *G01N 2001/005* (2013.01); *G01N 2001/4094* (2013.01)

(56) References Cited

U.S. PATENT DOCUMENTS

2010/0261157 A1 10/2010 Brock
2010/0291536 A1 11/2010 Viljoen et al.

CLOSED CIRCUIT STERILE DEVICE AND METHOD OF COLLECTION, TRANSPORT AND PROCESSING IN TOTAL STERILE CHAIN

BACKGROUND OF THE INVENTION

Field of the Invention

The present invention relates to a closed circuit sterile device and method of collection, transport and processing in total sterile chain.

More specifically, the invention concerns a medical-surgical sterile device, suitable for collecting and transporting from the surgery room to the clinical and microbiological analysis laboratory of human biological samples (body fluids, tissues, organs and portions thereof) and/or implantable or explanted prosthetic materials during surgeries (such as, by way of example, but not limited thereto, joint replacements or their parts or components, metal plates, wires, cerclage, screws, nails, staples, bone cement, bone substitutes, catheters, heart valves, breast implants, urological implants, neurosurgical implants and osteosynthesis materials, dentures or maxillofacial prostheses, etc.), so as to totally preserve them from bacterial contamination.

In the following, the description will be directed to the collection and the transport of an explanted prosthesis or biological samples, but it is clear that it must not be considered limited to these specific uses.

Brief Discussion of the Related Art

As it is well known, at present the market for implanted biomaterials, in particular directed to the orthopedics and traumatology medical fields, is presenting a very high development, due to the number of patients steadily increasing.

It is also well known that bacterial infections related to the installation or the removal of such biomaterials are the most dangerous complication in said orthopedics and traumatology fields, with their associated high social and economic costs.

Bacterial infection is, then, in any case, a very dangerous complication also in the fields of neurosurgery, in cardiovascular medicine, in urology, in plastic surgery and in general surgery.

The detection of bacteria, when carried out, for example, on human biological samples (biological fluids, tissues, organs and portions thereof) and/or implantable materials or prosthetic explanted during of surgical procedures (e.g., but not limited thereto, joint replacements or their parts or components, metal plates, wires, cerclage, screws, nails, staples, bone cement, bone substitutes, catheters, heart valves, breast implants, urological implants, neurosurgical implants and osteosynthesis materials, dentures or maxillofacial prostheses, etc.) is also essential to confirm any diagnosis, as well as to allow, therefore, the determination of the most appropriate antibiotic treatment, which, in such cases, can even extend for several weeks or months.

Generally, to detect any bacteria, for example in an explanted prosthesis, it has to be transported in a suitable analysis laboratory, away from the surgery room, by means of a sterile container, to be extracted out of the container, once arrived at the laboratory analysis, and performing, thus, the analysis operations.

To extract bacteria from prostheses different processes are known. A first process is known as sonication, and it uses a mechanical instrument to remove bacteria from the implants or prostheses. That system is effective to increase the rate of isolation of the bacterial biofilm. However, such technology is rather long in the application, as well as expensive, as it requires specially trained personnel. These limits imply the use only in a reduced number of hospitals.

Recently it has been proposed and developed a system of chemical detachment of bacteria from prosthetic implants in vitro. This technique is effective as the sonication, but it has a low cost and a remarkable ease of use. Such chemical extraction is obtained by treating the biomaterial implanted with a dithiothreitol (DTT) solution.

As it is easy to understand, the main risk of bacterial detection procedures is that the prosthesis or the biological material to be collected for the examination is contaminated during the transport phase or the extraction of the same from the container intended to protect and transport the same, since, in that case, there would be a so called "false positive", i.e. a prosthesis contaminated by bacteria not of the surgical site (i.e. by those bacteria which existence is really desired to detect), but exogenous. This could lead a patient to be subjected to a preventive antibiotic treatment, without a real need.

It appears evident that this procedure is subject to high risks for the patient.

The patent application US2010/261157 A1, U.S. Pat. No. 3,163,160 A and U.S. Pat. No. 5,869,003 A are known in the art.

The first patent application relates to a container having two compartments, separated by a barrier, in one of which a swab can be inserted and in the other there is a processing fluid. The swab may be inserted in the other compartment, for obtaining a sample to be analyzed. The problem of the described solution is that it does not allow multiple withdrawals of the solution without contamination risk.

The patent application U.S. Pat. No. 3,163,160 A is a system similar to the previous one, but in this case it is the processing liquid that passes into the compartment in which the swab is placed. Also in this case, it is not possible to perform with certainty multiple withdrawals of the solution without risk of contamination.

Finally, the patent application U.S. Pat. No. 5,869,003 A relates to a diagnostic kit, which comprises a material strip with diagnostic reagent, that when contacting a swab in a sterile compartment, allows to detect the infection status of the biological material on the swab.

BRIEF SUMMARY OF THE INVENTION

In light of the above, it is, therefore, object of the present invention providing a medical use closed circuit sterile device and a collection and sterilization method, capable to overcome the limitations of the prior art, reducing the contamination risks.

Another object of the invention is to provide a device, which allows bacterial identification in a simple and economically sustainable way.

It is therefore specific object of the present invention a sterile closed loop device for medical-surgical use intended for the collection, the transportation and the processing of prostheses and/or biological samples and the like, having at least one collection compartment provided with an hermetically closable main opening, for the introduction of said prosthesis and/or biological samples and the like to be analyzed, so as to be contained in it, at least one containment chamber, in which a solution is contained for the chemical detachment of bacteria adhering to animate or inanimate surfaces, such as prostheses and the like, and/or bacterial biofilm, said containment chamber being selectively communicating with said collection compartment, so that said solution can be conveyed from said containment chamber to said collection compartment, for the chemical separation of bacteria to said prosthesis and/or biological samples and the like to be analyzed, that can be inserted in said collection compartment, and extraction means of said solution for the chemical detachment of bacteria from said collection compartment.

Always according to the invention, said solution for the chemical detachment of bacteria and/or bacterial biofilm could comprise a solution of dithiothreitol (DTT) and/or N-acetylcysteine and/or glutathione and/or other thiol derivatives in concentrations between 0.0001% and 100%, said solution being capable of dissolving the matrix of the biofilm allowing the isolation and consequently the bacteria identification.

Still according to the invention, said collection compartment could contain inside culture medium to allow the growth of aerobic microorganisms, including bacteria, fungi, mycoplasma and protozoans and the like, and/or reducing agents, to enable the growth of microorganisms under anaerobic conditions, so as to allow the analysis of germs and/or biofilms produced by aerobic and/or anaerobic bacteria.

Further according to the invention, said device could comprise an additional containment chamber for containing the culture medium, selectively communicating with said collection compartment, said culture medium being adapted to allow the growth of aerobic microorganisms, including bacteria, fungi, mycoplasma and protozoa and the like, and/or reducing substances, to allow the growth of microorganisms under anaerobic conditions.

Advantageously according to the invention, said collection compartment could comprise inside resins or similar chemical substances, capable of removing the antibiotics possibly present on said prosthesis and/or biological samples and the like to be analyzed.

Always according to the invention, said device could have a plurality of collection compartments, each selectively communicating with said at least one containment chamber.

Still according to the invention, said device could have a plurality of collection compartments, each selectively communicating with a respective containment chamber.

Advantageously according to the invention, said collection compartment and said containment chamber could be made of soft material and/or compressible.

Further according to the invention, said containment chamber could be arranged inside said compartment collection.

Always according to the invention, said device could comprise a valve interposed between said collection compartment and said containment chamber, adapted to allow the passage of said solution for the chemical detachment of bacteria from said containment chamber to said collection compartment, said valve being provided with a stem that can be open by breaking, with selective passage in one direction.

Still according to the invention, said device could comprise at least one duct and a tap interposed between said collection compartment and said containment chamber, adapted to allow the passage of said solution for the chemical detachment of bacteria, from said containment chamber to said collection compartment.

Advantageously according to the invention, said device could have a first opening communicating with said collection compartment, on which a respective connector is installed, with which said extraction means are connected.

Further according to the invention, said device could have a second opening, provided with a respective connector said chemical solution for the detachment of bacteria and/or bacterial biofilm.

Always according to the invention, said collection compartment could comprise means for hermetic closure, such as a double sided tape or the like or by heat sealing, and a facilitated opening to facilitate the maintenance of the sterility.

Advantageously according to the invention, said extraction means could comprise a conduit connected with said collection compartment, and a sampling device or holder, selectively closable connected with said conduit, a syringe with or without needle or a system type "luer-lock" or a vacutainer or membranes that can be perforated being connectable to said sampling device or holder.

Always according to the invention, said extraction means could comprise a filter, connected between said collection compartment and said sampling device for the test tube or holder, adapted to filter the biological material of the patient, such as residues of processed sample material.

It is further object of the present invention a method for collecting, transporting and processing a prosthesis and/or biological samples and the like to be analyzed, comprising the following steps: (A) providing a device as defined above; (B) inserting said prosthesis and/or biological samples and the like to be analyzed into said device; (C) conveying said solution for the chemical separation of bacteria from said containment chamber to said collection compartment, so that said chemical solution for the detachment of bacteria contacts said prosthesis and/or biological samples and the like to be analyzed; and (D) extracting said solution for the chemical detachment of bacteria from said collection compartment by said extraction means.

Always according to the invention, said extraction step (D) could comprise the step of filtering said chemical solution for the detachment of bacteria, so as to filter biological material.

Still according to the invention, said step (C) comprises the step of compressing said containment chamber, to allow the passage of said solution for chemical detachment of bacteria from said containment chamber to said collection compartment.

Advantageously according to the invention, said method could comprise, between said steps (C) and (D), the step of inserting said container in a sonicator or a mechanical shaker, for increasing the detachment of bacteria adherent to the biofilm on explanted materials.

Further according to the invention, said method could provide the possibility of simultaneously inserting multiple samples taken from the same patient within the same device to enable an effective diagnosis, optimizing time and costs.

BRIEF DESCRIPTION OF THE DRAWINGS

The present invention will be now described, for illustrative but not limitative purposes, according to its preferred embodiments, with particular reference to the figures of the enclosed drawings, wherein.

DETAILED DISCUSSION OF THE PREFERRED EMBODIMENTS

In the various figures, similar parts will be indicated by the same reference numbers.

Figure 1:
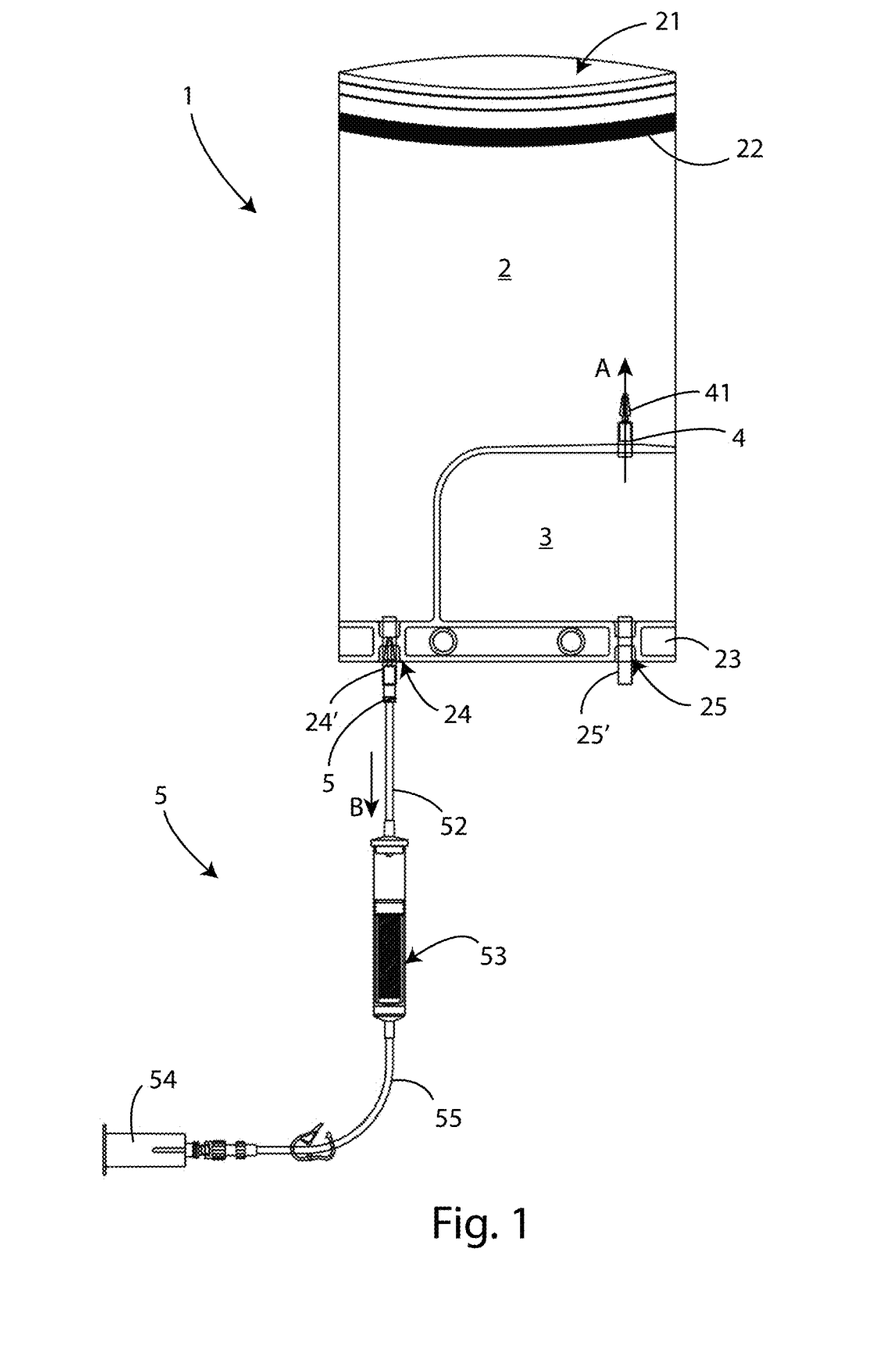
FIG. 1 shows a first embodiment of the device for medical use according to the present invention.

Referring to FIG. 1 a first embodiment of a closed circuit sterile device 1 for medical-surgical use is shown.

Said device 1 comprises a collection compartment 2, having an opening 21, and a containment chamber 3.

Said collection compartment 2 comprises closing means, such as a double-sided tape 22 and the like or by heat sealing, to removably close said opening 21.

Associated with said collection compartment 2 a bottom junction line 23 is also provided, on which a first opening 24 is formed, communicating with said collection compartment 2, and a second opening 25 is formed, communicating with said containment chamber 3. On each one of said openings 24 and 25 a respective first 24' and second 25' connector is installed, which can be of conical type. The function of said connectors 24' and 25' will be better defined below.

On said junction line 23 a hook (not shown in the figure) is also provided, whose function will be better explained below.

Said containment chamber 3 is arranged, in this embodiment, so as to be contained in said collection compartment 2. In addition, said containment chamber 3 contains a solution or fluid, in general, for the chemical detachment of bacteria and/or bacterial biofilm, as a solution of dithiothreitol (DTT) and/or N-acetyl-cysteine and/or glutathione and/or other thiol derivatives at concentrations between 0.0001% and 100%. Said second opening 25 and the connector 25' are used in the production phase for filling said containment chamber 3 of said solution for the chemical detachment of bacteria and/or bacterial biofilm.

The device 1 also comprises a valve 4 interposed between said collection compartment 2 and said containment chamber 3, provided with a opening stem 41, with selective passage in one direction of the liquid.

The two compartments 2 and 3 are realized by means of a non-rigid material.

To said device 1, extraction means 5 are coupled, which comprise an extraction connector 51, that can be coupled with said first connector 24' of said device 1, connected by a duct 52 to a filter 53, adapted to filter the biological material, as it will be better defined below, and a pickup device for tube or holder 54, which is also connected by means of a further duct 55 to said filter 53.

The operation of the sterile device 1 for medical use described above is as follows.

Said device 1 is presented ready for use with said containment chamber 3 filled with said solution for the chemical detachment of bacteria and/or bacterial biofilm, filled in a sterile way by suitable means through said connector 25'.

When it is necessary to insert, for example, a prosthesis explanted in the surgery room, said prosthesis is inserted through said opening 21 in said compartment 2, so as to be transported from the surgery room to an analysis center. Then, when it is necessary to verify the presence or absence of bacteria in said prosthesis, the valve 4 is opened, by breaking said stem 41. This can easily be carried out by acting on the valve 4 itself from the outside, due to the fact that the compartment 2 is made, as said, by soft material. When the valve 4 is opened and the containment chamber 3 is compressed manually, the solution for the chemical detachment of bacteria and/or bacterial biofilm passes from said containment chamber 3 to said collection compartment 2, as shown by arrow A, thus entering in contact with the prosthesis contained in said collection compartment 2.

To allow the passage of the solution for the chemical detachment of bacteria from said containment chamber 3 to the collection compartment 2, it is possible to hang said device 1 turned upside down by means of said hook arranged on said junction line 23.

Also, due to the fact that said collection compartment 2 is made of soft material, an operator can allow, by manually moving said collection compartment 2, the solution for the chemical detachment of bacteria and/or bacterial biofilm to come into contact with the entire surface of the explanted prosthesis, so that said solution carries out a chemical detachment of bacteria that are found on the prosthesis, so as to make them more isolable and identifiable.

Finally, said extraction means 5 are coupled to said first connector 24', so that the solution for the chemical detachment of bacteria and/or bacterial biofilm, together with the bacteria detached from said prosthesis, is conveyed (see arrow B) towards said holder 54, passing through said filter 53, which is adapted to filter any biological materials of the patient, such as material residues of the sample processed, remained on the prosthesis after the explantation and present in the solution for the chemical detachment of bacteria and/or bacterial biofilm. In this way, DTT solution can be collected by means of a test tube (not shown in the figure) by means of said holder 54.

The described device 1 can also be of disposable type.

FIGS. 2-7 show a device for sterile medical use 1', which is not part of the present invention.

In this case, as it can be seen, said device 1' is rigid and the collection compartment 2, in which the prosthesis P can be placed through the opening 21', is hermetically closable by a door 22', provided with a respective closure 22". The containment chamber 3 is obtained in a further container 3' made of flexible material, which is contained in a tray 6, removed from the device 1' and arranged below said collection compartment 2.

Said further container 3' is made of flexible material, i.e. not rigid and, also in this case, it is filled with a solution for the chemical detachment of bacteria and/or bacterial biofilm. Said collection compartment 2 and said containment chamber 3 are connected through a valve 42 and a conduit 43.

Said further container 3' can possibly be exchangeable, allowing, once sterilized, to recover the device 1' after use.

Moreover, said device 1' comprises, also in this case, extraction means 5, having a holder 54 for the tube or vacutainer, connected by a conduit 52 to a valve 56, of one-way pressure type, the operation of which will be better explained in the following.

Figures 2, 3:
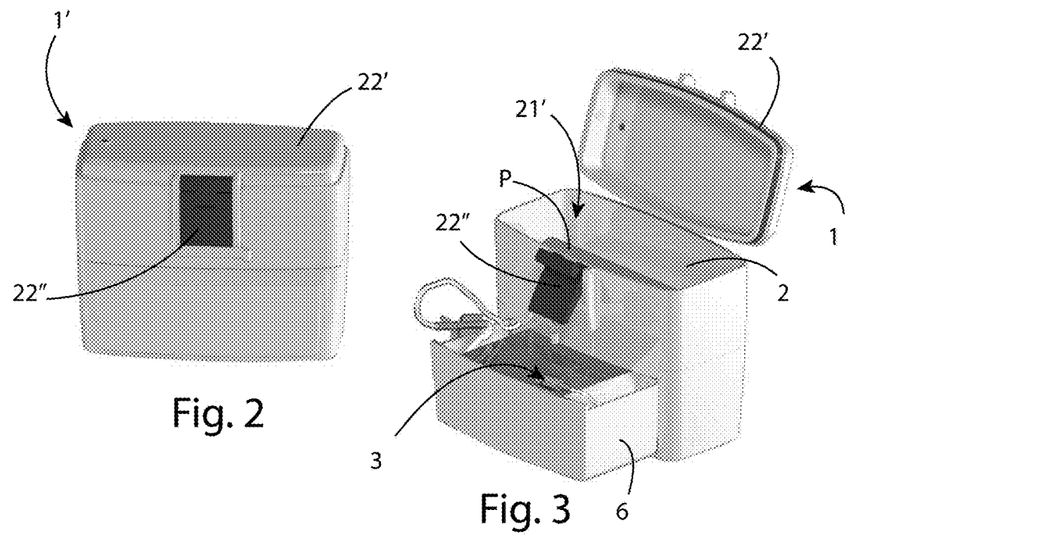
FIG. 2 shows a front perspective view of a device for medical use, which is not part of the present invention.
FIG. 3 shows a perspective view of the device according to FIG. 2 in the open position.
Figure 4:
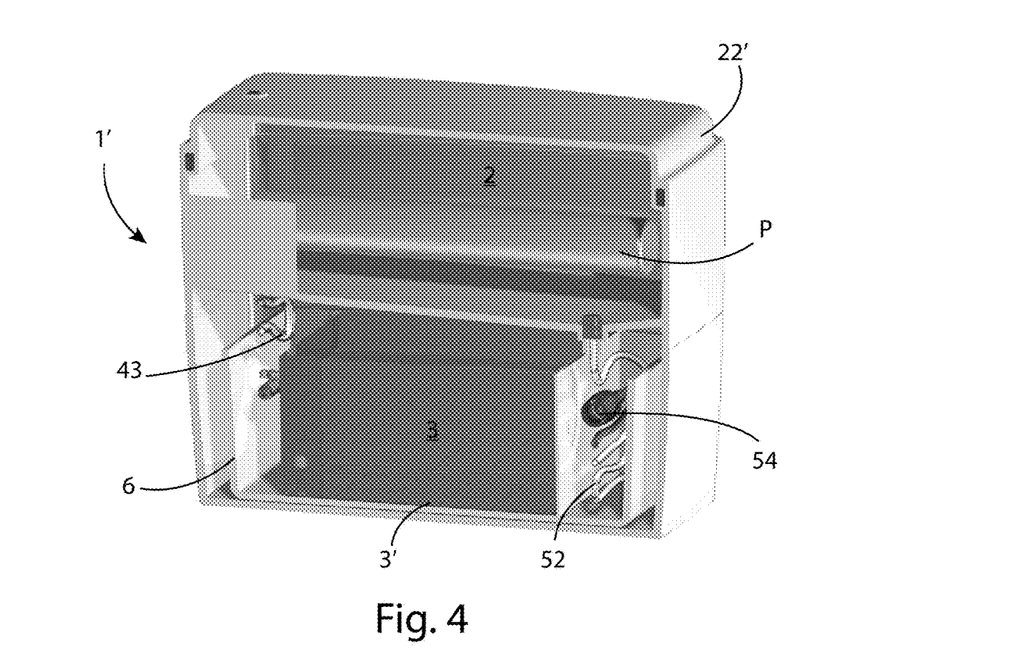
FIG. 4 shows a longitudinal section of the device according to FIG. 2.
Figure 5:
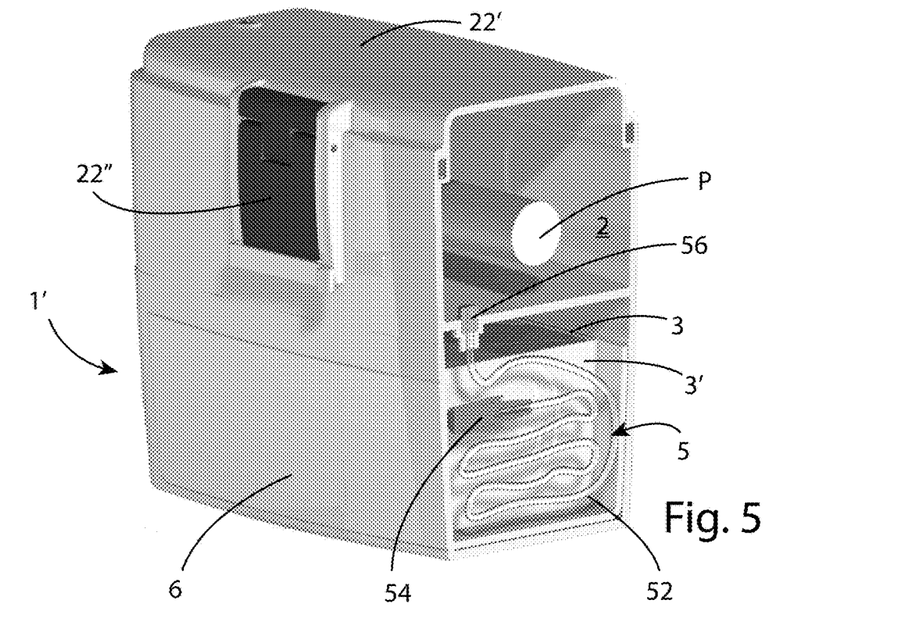
FIG. 5 shows a first cross sectional view of the device according to FIG. 2.
Figure 6:
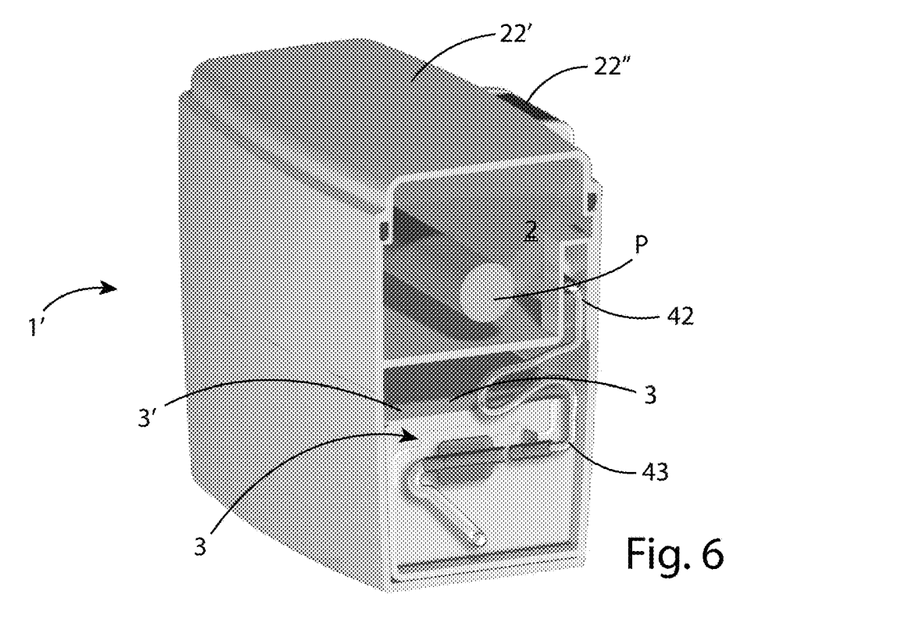
FIG. 6 shows a second cross sectional view of the device according to FIG. 2.
Figure 7:
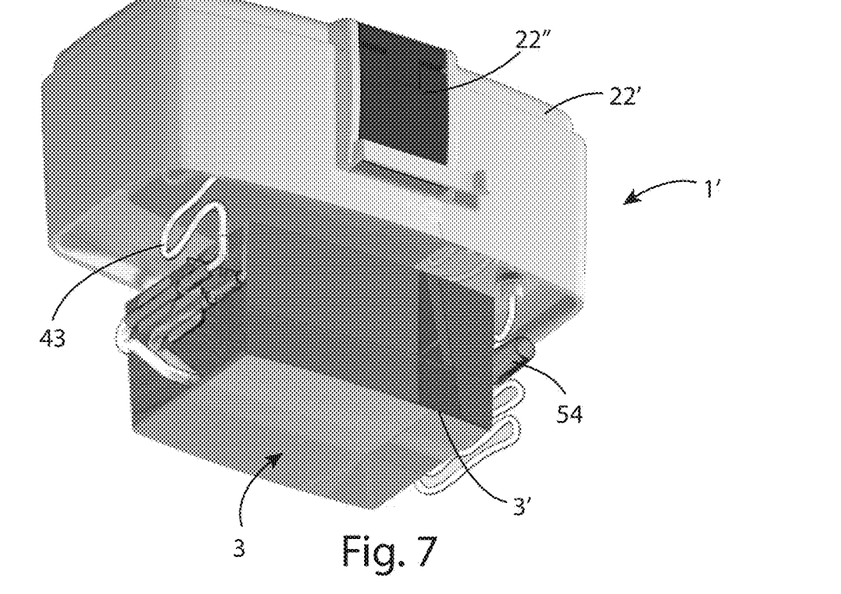
FIG. 7 shows a partially exploded view of the device according to FIG. 2.

The operation of the sterile device 1' for medical use described above is carried out in a way similar to that of the device 1 shown in FIG. 1.

In particular, the prosthesis P or the biological material to be preserved is placed, when in surgery room, within the collection compartment 2, which is subsequently closed by the door 22'.

After the transport, containment chamber 3, already placed in the tray 6 or placeable therein, is connected by the conduit 43 to the collection compartment 2. By compressing the containment chamber 3, the solution for the chemical detachment of bacteria and/or bacterial biofilm passes through valve 42 and enters within collection compartment 2, thus contacting with the prosthesis P or the biological material contained therein.

Once said solution carries out the chemical detachment of bacteria found on the prosthesis P, for extracting said solution, now possibly charged of bacteria, it is sufficient to couple a test tube or vacutainer in the holder 54, to perform the extraction of the solution with a syringe with or without needle or by means of a "luer-lock" type system or vacutainer or membranes that can be perforated, so as to overcome the resistance of the closure valve 56.

Figure 8:
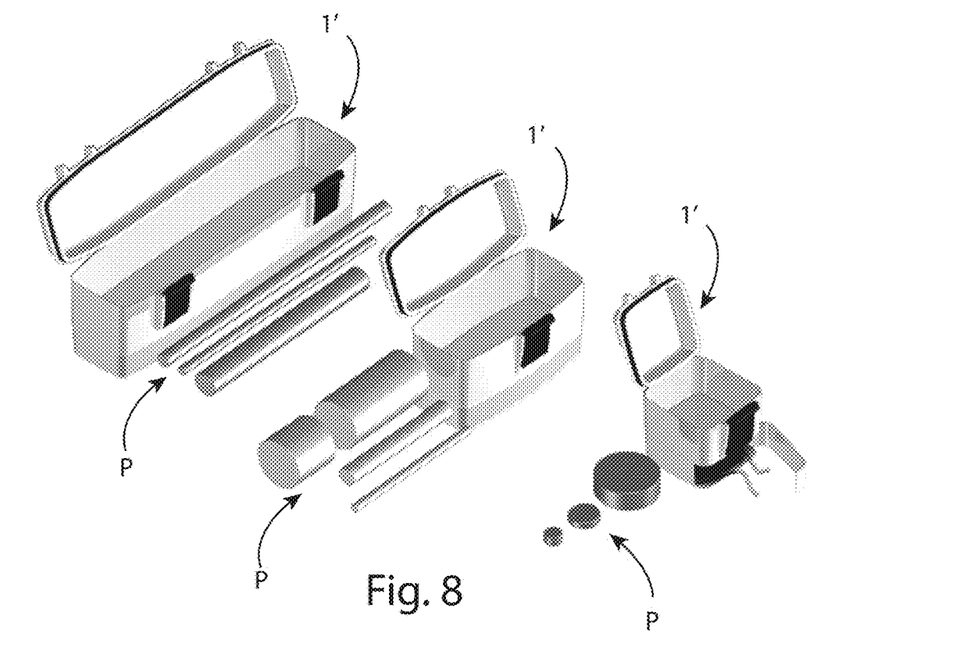
FIG. 8 shows a perspective view of three containers according to FIG. 2, of different measures.

FIG. 8 shows, finally, for completeness, three containers 1' of various measures, intended to contain different types of prosthesis, distinguished for size and shape.

In further embodiments according to the invention, said device 1 may comprise a plurality of collection compartments 2, for the collection of multiple samples in a separate and independent way. These collection compartments 2 can all be connected to a single common containment chamber 3, or a respective containment chamber 3 can be provided for each collection compartment 2.

In further embodiments of the device 1 according to the invention, said collection compartment 2 can contain inside the culture medium, to allow the growth of aerobic microorganisms, including bacteria, fungi, mycoplasma and protozoa, and/or reducing substances, so as to allow the growth of microorganisms under anaerobic conditions.

Container 1 according to the invention can be placed in a sonicator or a mechanical shaker, to increase the detachment of bacteria, which adhere to the biofilm on the explanted materials.

Furthermore, the container 1 according to the invention allows storage of samples explanted and contained therein at temperatures between −20° and +90° and preferably between −20° and +50°.

An advantage of the invention is the increase of bacterial recovery from the biological sample/material introduced into the device, allowing to increase the sensitivity, specificity, negative predictive value and positive than the methods currently in use.

Another advantage of the present invention is that the device according to the invention provides for the possibility to process the samples within 24/48 hours after the explantation without the need of a temperature-controlled storage.

It is an advantage of the present invention the fact that the solution is capable of dissolving the biofilm matrix allowing the isolation and consequently the identification of bacteria more effectively as compared to procedures commonly used in the laboratory.

A further advantage of the device according to the present invention is to provide a hermetic seal, capable of preventing the accidental spillage of the collected material and of the chemical substances.

It is also advantage of the device according to the present invention the fact of being particularly inexpensive with respect to solutions according to the prior art.

A further advantage of the device according to the present invention is that it is used also in veterinary field.

The present invention has been described for illustrative but not limitative purposes, according to its preferred embodiments, but it is to be understood that modifications and/or changes can be introduced by those skilled in the art without departing from the relevant scope as defined in the enclosed claims.

The invention claimed is:

1. A sterile closed loop device for medical-surgical use intended for the collection, the transportation and the processing of prostheses and/or implantable or explanted prothesic materials, the device comprising:
   at least one collection compartment provided with an hermetically closable main opening, for the introduction of said prosthesis and/or implantable or explanted prothesic materials to be analyzed, so as to be contained in said compartment,
   at least one containment chamber, in which a solution is contained, filled in a sterile way by suitable means through a connector, for the chemical detachment of bacteria adhering to animate or inanimate surfaces, said containment chamber being selectively communicating with said collection compartment, so that said solution can be conveyed from said containment chamber to said collection compartment, for the chemical separation of bacteria to said prosthesis and/or implantable or explanted prothesic materials to be analyzed, that can be inserted in said collection compartment,
   extraction means of said solution for the chemical detachment of bacteria from said collection compartment, and
   a valve interposed between said collection compartment and said containment chamber, adapted to allow the passage of said solution for the chemical detachment of bacteria from said containment chamber to said collection compartment, said valve being provided with a stem that can be opened by breaking,
   wherein said solution for the chemical detachment of bacteria and/or bacterial biofilm comprises a solution of dithiothreitol (DTT) and/or N-acetylcysteine and/or glutathione and/or other thiol derivatives in concentrations between 0.0001% and 100%, said solution being capable of dissolving the biofilm matrix allowing the isolation and consequently the bacteria identification,
   wherein said valve provides with selective passage in one direction, and
   wherein said collection compartment and said containment chamber are made of soft and/or compressible material, in such way that, when the valve is opened and the containment chamber is manually compressed, the solution for the chemical detachment of bacteria and/or bacterial biofilm passes from said containment chamber to said collection compartment, thus entering in contact with the said prosthesis and/or implantable or explanted prothesic materials contained in said collection compartment.

2. The device according to claim 1, wherein said collection compartment contains inside culture medium to allow the growth of aerobic microorganisms, including bacteria, fungi, mycoplasma and protozoans, and/or reducing agents, to enable the growth of microorganisms under anaerobic conditions, so as to allow the analysis of germs and/or biofilms produced by aerobic and/or anaerobic bacteria.

3. The device according to claim 1, wherein said device comprises an additional containment chamber for containing the culture medium, selectively communicating with said collection compartment, said culture medium being adapted to allow the growth of aerobic microorganisms, including bacteria, fungi, mycoplasma and protozoa, and/or reducing substances, to allow the growth of microorganisms under anaerobic conditions.

4. The device according to claim 1, wherein said collection compartment comprises inside resins or similar chemical substances, capable of removing the antibiotics possibly present on said prosthesis and/or biological samples to be analyzed.

5. The device according to claim 1, wherein said device has a plurality of collection compartments, each selectively communicating with said at least one containment chamber.

6. The device according to claim 1, wherein said device has a plurality of collection compartments, each selectively communicating with a respective containment chamber.

7. The device according to claim 1, wherein said containment chamber is arranged inside said collection compartment.

8. The device according to claim 1, wherein said device comprises at least one duct and a tap interposed between said collection compartment and said containment chamber, adapted to allow the passage of said solution for the chemical detachment of bacteria, from said containment chamber to said collection compartment.

9. The device according to claim 1, wherein said device has a first opening communicating with said collection compartment, on which a respective connector is installed, with which said extraction means are connected.

10. The device according to claim 1, wherein said device has a second opening, provided with said respective connector, for filling in the production phase said containment chamber with said chemical solution for the detachment of bacteria and/or bacterial biofilm.

11. The device according to claim 1, wherein said collection compartment comprises means for hermetic closure, and a facilitated opening to facilitate the maintenance of the sterility.

12. The device according to claim 1, wherein said extraction means comprise a conduit connected with said collection compartment, and a sampling device or holder, selectively closable connected with said conduit, a syringe with or without needle or a system type "luer-lock" or a vacutainer or membranes that can be perforated being connectable to said sampling device or holder.

13. The device according to claim 12, wherein said extraction means comprise a filter, connected between said collection compartment and said sampling device for the test tube or holder, adapted to filter the biological material of the patient.

14. A method for collecting, transporting and processing a prosthesis and/or implantable or explanted prothesic materials to be analyzed, comprising the following steps:
    (A) providing a device according to claim 1;
    (B) inserting said prosthesis and/or biological samples to be analyzed into said device;
    (C) conveying said solution for the chemical separation of bacteria from said containment chamber to said collection compartment, so that said chemical solution for the detachment of bacteria contacts said prosthesis and/or biological samples to be analyzed; and
    (D) extracting said solution for the chemical detachment of bacteria from said collection compartment by said extraction means.

15. The method according to claim 14, wherein said extraction step (D) comprises the step of filtering said chemical solution for the detachment of bacteria, so as to filter biological material.

16. The method according to claim 14, wherein said step (C) comprises the step of compressing said containment chamber, to allow the passage of said solution for chemical detachment of bacteria from said containment chamber to said collection compartment.

17. The method according to claim 14, wherein said method comprises, between said steps (C) and (D), the step of inserting said container in a sonicator or a mechanical shaker, for increasing the detachment of bacteria adherent to the biofilm on explanted materials.

18. The method according to claim 14, wherein said method provides the possibility of simultaneously inserting multiple samples taken from the same patient within the same device to enable an effective diagnosis, optimizing time and costs.

* * * * *